United States Patent
Schulte Eistrup et al.

(10) Patent No.: US 6,752,602 B2
(45) Date of Patent: Jun. 22, 2004

(54) BLOOD PUMP

(75) Inventors: Sebastian Schulte Eistrup, Herzebrock-Clarholz (DE); Catrin Bludszuweit, Rostock (DE)

(73) Assignee: Krankenhausbetriebsgesellschaft Bad Oeynhausen mbH, Bad Oeynhausen (DE)

( * ) Notice: Subject to any disclaimer, the term of this patent is extended or adjusted under 35 U.S.C. 154(b) by 0 days.

(21) Appl. No.: 10/220,357

(22) PCT Filed: Mar. 5, 2001

(86) PCT No.: PCT/EP01/02480

§ 371 (c)(1),
(2), (4) Date: Jan. 17, 2003

(87) PCT Pub. No.: WO01/66170

PCT Pub. Date: Sep. 13, 2001

(65) Prior Publication Data

US 2003/0147754 A1 Aug. 7, 2003

(30) Foreign Application Priority Data

Mar. 4, 2000 (DE) ..................................... 200 04 136 U (51) Int. Cl.[7] .............................. F04B 35/04; F01D 3/02
(52) U.S. Cl. ............... 417/356; 417/423.1; 417/423.12; 604/151; 415/102; 415/111; 415/170.1; 415/900

(58) Field of Search .............................. 417/356, 423.1, 417/423.12, 423.13; 604/151; 415/111, 112, 102, 170.1, 229, 900

(56) References Cited

U.S. PATENT DOCUMENTS

| | | | | |
|---|---|---|---|---|
| 4,994,078 A | * | 2/1991 | Jarvik | 623/3.14 |
| 5,055,005 A | * | 10/1991 | Kletschka | 417/356 |
| 5,195,877 A | * | 3/1993 | Kletschka | 417/356 |
| 5,507,629 A | * | 4/1996 | Jarvik | 417/423.3 |
| 5,713,730 A | | 2/1998 | Nose et al. | |
| 5,924,848 A | | 7/1999 | Izraelev | |
| 5,924,975 A | * | 7/1999 | Goldowsky | 600/16 |
| 5,951,263 A | * | 9/1999 | Taylor et al. | 417/356 |
| 6,135,710 A | * | 10/2000 | Araki et al. | 415/206 |

* cited by examiner

Primary Examiner—Charles G. Freay
(74) Attorney, Agent, or Firm—Bachman & LaPointe, P.C.

(57) ABSTRACT

The invention concerns a blood pump, in particular a ventricular cardiac support pump, with formed in a pump housing a blood chamber which is designed to hold a rotor rotatable about a rotor axis and at opposite ends in sections forms an inlet connectable with an inlet cannula, where an outlet from the blood chamber connectable with an outlet cannula extends in a direction perpendicular to the rotor axis, and where the rotor axis at its ends is mounted rotatably in mechanically active bearings provided in the area of the inlet concerned and connected with the pump housing.

6 Claims, 7 Drawing Sheets

BLOOD PUMP

The present invention relates to a blood pump, in particular a ventricular cardiac support pump, according to the preamble of claim 1.

For the treatment of cardiac insufficiency, as well as conservative medication-based approaches, various surgical treatments have been developed from the replacement or reconstruction of heart valves via electrical stimulation of the cardiac muscle through to heart transplant. Because of the limited availability of the required donor hearts and the growing waiting lists however, the latter treatment option—which in critical cases however offers the greatest possible potential treatment success—can only benefit a low number of patients. Annually 20 to 30% of patients on the waiting list for heart transplants die before a suitable donor organ can be found.

The (temporary) support of insufficient circulation by ventricular assistance devices (VAD), such as suitable cardiac support pumps, dates back to the beginning of the 70s and is today an established concept successfully applied in many transplant centres. As well as devices to assist the left ventricle (LVAD), in particular also devices are available to assist both diseased ventricles of the heart (BVAD). Such systems are sometimes implanted totally intracorporeal so that the patient can continue to be treated as an out-patient and in particular while awaiting a transplant is no longer tied to the hospital as an in-patient.

In concrete terms ventricular assistance devices constitute an extracardial bypass as they pump blood from the left ventricle into the rising aorta. As a result the load on the left ventricle is reduced. If correspondingly the right ventricle is also insufficient, a pump bypassing this must be fitted accordingly. VAD are in principle placed so that the native heart remains in situ, in contrast to artificial hearts.

Recent scientific publications show that a damaged cardiac muscle on which however the load is relieved by VAD has the ability to regenerate; in some cases no transplant is required and the VAD can be removed.

Ventricular support systems of the known type are in principle divided into pumps with pulsatile flow and those with continuous flow. Pulsatile cardiac support pumps simulate the native heart in function and rhythm and in an action cycle produce both a filling and an expulsion phase for blood by means of a blood chamber which typically consists of an elastic plastic bag, where valves ensure a directed blood flow. Such systems have proved clinically successful and allow the support of patients for periods of up to around two years. Nonetheless pulsatile cardiac support systems have some disadvantages. These VAD are usually bulky and are difficult to implant without problems in the patient's body. The efficiency of pulsatile VAD is also very low due to the complex drive mechanism, and the drive and control system is complex and hence particularly susceptible to fault in long-term implantation. Above all however the long contact time of the blood during the filling phase leads to more thromboses which then carry a risk of central embolism with neurological failure or similar; this risk of thrombosis is supported by the turbulence occurring at the valves with increased shear stress in the blood flow.

Non-pulsatile VAD in contrast to the technology described above generate a continuous blood flow and require a relatively small blood chamber without elastic lining and cardiac valves. Accordingly the size of the support pump can be reduced considerably which makes it accessible to a larger patient group. There is also a considerably reduced risk of thrombosis due to the absence of an elastic membrane in the blood chamber and cardiac valves. As also the drive system of non-pulsatile VAD is simple and efficient, conventional brush-free DC motors are used with an energy consumption of less than 8 Watt, which is low.

The non-pulsatile circulation support however brings other difficulties. Due to the absence of cardiac valves (which allow directed blood flow) in the case of pump failure there is a risk of recirculating blood, which risk must be eliminated by additional measures. The output of a non-pulsatile VAD is also difficult to determine as there is no blood chamber with defined volume, so more precise information on the output can only be given by precise flow measurements (with an implanted flow meter for example).

Non-pulsatile blood pumps can be divided into centrifugal and axial pumps, where technologically the latter currently play no great role in practical clinical use, so only the centrifugal pumps are discussed below as the relevant state of the art (and as the genus for the present invention).

Commercial centrifugal pumps for cardiac support accelerate the blood perpendicular to the direction of the incoming blood flow and usually have a conical blood chamber in which is rotatably suspended a rotor (usually magnetically coupled). Traditionally the blood is supplied to the tip of the blood chamber through an inlet cannula, distributed evenly over the rotor and accelerated centrifugally, and blood leaves the blood chamber in the area of the greatest pressure and greatest speed through an outlet channel with an axis usually perpendicular to the rotor axis. The blood is usually accelerated by rotor blades provided on the rotor. However in such known centrifugal pumps with conical blood chamber, there is a relatively complex flow pattern of the transported blood with an inverse pressure ratio on the back of the rotor, with the risk that precisely in the area of the rotor shaft (the term "shaft" in the context of the present application is synonymous with "axis" and used accordingly), there is a risk of thrombosis formation at its mounting or on the rotor top. Thus a thrombus growing on the pump shaft would be able to grow in the peripheral direction and lead to a continuous increase in friction with a clearly increased energy consumption and the risk of pump arrest; in addition there is a risk of emerging thrombus or embolism formation in the patients system.

U.S. Pat. No. 5,924,848 discloses a generic blood pump with the features in the preamble of claim 1, where here the blood chamber, in contrast to the state of the art described above, is formed as a double cone with two opposing inlets at the relevant tips of the double cone. This technologically has a rotor which can rotate without bearings in the blood chamber of the pump housing and is held in position by hydrodynamic forces. As the inventor explains, such a solution as well as ensuring increased efficiency in particular avoids the problem of mounting and again the resultant thrombosis formation etc.

However this known solution too does not appear optimum and in particular in practical clinical use, under changing conditions of use, is potentially problematic. Namely it can be assumed that any position changes of a patient (with an implanted pump) lead to pressure changes and hence flow changes at the inlets of the pump and to not inconsiderable mechanical stresses on the rotor; due to the (efficiency-related) short distances between the tips of the rotor blades and the pump housing (approximately 1 to 3 mm) the rotor can easily collide with the internal pump housing with the risk of damage, increased wear and failure.

The object of the present invention is therefore to improve a known blood pump, in particular for ventricular cardiac support, in that the practical operating properties are improved in relation to known pump solutions, in particular the suitability for various operating and patient conditions is increased and the risk of harmful thrombosis formation can be reduced. At the same time a new pump to be created is characterised by low wear, high reliability and low energy consumption.

This task is solved by the blood pump with the features of claim 1; advantageous refinements of the invention are described in the sub-claims.

According to the invention it is provided that the rotor axis (rotor shaft) is rotatably mounted at the ends in mechanically active bearings, where in each case the mounting on the pump housing is located in the area of the opposing inlets. In other words according to the invention the rotor shaft is fixed mounted in the area of the incoming blood so that an opposing stream of incoming blood acts on each mounted end of the rotor shaft. According to the invention and advantageously this leads to there being practically no axial load on the bearings in the ideal state as an axial force exerted on the rotor (or the rotor shaft) by the incoming blood in a first inlet is compensated by the opposite force generated by the incoming blood in the second inlet. As a result (compared with the state of the art, where blood flowing in on one side at a cone tip places considerable load on the conventional bearings due to axial force), there is an extremely low susceptibility to wear so that a long life and low fault susceptibility of the bearing principle according to the invention can be assumed. At the same time however the present invention avoids the incalculable factors and the risk of fault by a bearing-free suspension of the rotor as in the generic U.S. Pat. No. 5,924,848, and—in the case of a purely mechanical bearing without magnetic support—additional electrical energy consumption.

Irrespective of this, as part of a possible refinement it is proposed to support the bearings which are primarily active mechanically according to the invention with magnets (permanent or electromagnets), where it is possible for example by suitable dimensioning of the mechanical mounting to guide the rotor axis in a primarily magnetically active manner (accordingly with low friction or wear) but at the same time however as before to utilise the existing mechanical bearings when, due to vibrations or other states which are potentially problematical for purely magnetic bearings, the rotor is moved from a stationary central position so that in this case the mechanically active bearing has a safety effect.

According to a refinement it is proposed to structure the blood flow through the pump carefully and extremely efficiently, although with low turbulence and avoiding possible shear forces on the blood flow (which cause the risk of thrombosis formation).

Firstly this is achieved by suitable design of the inlet and outlet geometry so that the cross-section area decisive for a flow speed at the inlets is larger than the corresponding cross-section area of the outlet (whereas in contrast naturally the cross-section area of the outlet connector must be equal to the area of the intraventricular singular supply connected before the pump). Due to the enlargement of the inlet cross-section according to a refinement, namely the blood flow is slowed down with the result that less blood trauma occurs at the inlet and at the rotor surface. Also, due to the design of the opposing inlets, the blood must be supplied through relatively long inlet cannulae which in turn cause a pressure fall.

In addition according to a refinement it is proposed in the inlets to provide means for flow control which preferably act to achieve prerotation, turbulence prevention or as flow regulator. As a result the risk of harmful thrombosis formation is reduced further where for example according to the invention suitably structured devices can be used for flow guidance, such as flow regulators, at the same time as reliable and efficient end suspension or mounting of the rotor (rotor shaft) in the context of the present invention. A further preferred refinement also provides that such mounting is flushed by incoming blood when a suitable projection, in particular of the nature of a flushing lip, guides part of the incoming blood into the bearing for flushing purposes.

As a further measure of the invention for the careful, low turbulence acceleration of the blood, it is provided as well as the rotor blades used for direct centrifugal acceleration, also to use the relative geometry between the pump interior and rotor body. More precisely the rotor body with its outer surface is structured such that an effective flow cross-section for flowing blood between the inlet and outlet diminishes in the direction of the outlet; for example this can be achieved in that a (where applicable) double-conical rotor body has a greater cone pitch than the surrounding walls of the blood chamber. This then leads to the incoming blood being moved additionally by shear forces on the rotor body and the total energy transfer of the rotor energy to the blood takes place with greater efficiency at low pressure; accordingly the rotor blades—in particular in the axial direction—can be reduced without reducing the overall efficiency of the pump. A reduction in size of the rotor blades (which further preferably are rounded at the ends in cross-section) again reduces the risk of blood damage, in particular avoiding the "mill" effect shown according to the state of the art in U.S. Pat. No. 5,924,848 (the rotor, largely terminating flush with the blood chamber, behaves like a mill for the incoming blood and can destroy blood constituents; at the same time blood is accelerated centrifugally in the inlet connector and can lead to filling obstacles, with reduced efficiency). Rather an acceleration-active rotor surface first begins at a certain predetermined distance from the relevant inlets so that the blood enters the blood chamber laminar and can flow parallel to the shaft. The result is a clearly reduced blood trauma, but due to the geometric design measures described above, also high efficiency of the pump system. In addition the flow regulators provided according to a refinement prevent a (rotor-induced) harmful centrifugal flow of the blood in the area of the inlets.

According to a further advantageous refinement the magnets necessary for drive of the rotor are arranged not on the rotor blades themselves e.g. at their tips, but in the rotor body. Due to such measures the balancing of the rotor in particular at high speeds is considerably simplified and the radial bearing load reduced; any efficiency losses are in turn compensated by the design measures described above in the rotor geometry designed for low turbulence. The advantage here is also that a rod magnet is provided which can preferably be arranged in the inside of the rotor body next to its outer surface and perpendicular to the axis of rotation, and extends for example from one outside surface to the opposite outside surface of the rotor body.

According to another advantageous refinement of the invention it is provided to encapsulate the mechanically active bearings with suitably designed housings where here preferably a housing form is selected which is adapted for favourable flow of the blood flowing into the inlets, utilising this for cooling the bearing concerned. The particularly preferred slide or roller bearings are in each case embedded in the bearing housing with good heat conduction which simultaneously serves for fixing the bearings, delimiting these from the flow area, and ensuring an optimum atraumatic flow round the bearings and heat dissipation from the bearings. The bearing housing is attached to the pump housing by means of flow control devices. The design of the bearing housing is such that there is little influence on the axial supply flow. The flow follows the shape of the bearing housing, tapering to a tip at the ends, without forming blood-damaging irregularities or stagnation areas. Such a design with slide or roller bearings within a bearing housing with good heat conduction can, as described above, be attached to the pump housing by means of suitably designed flow control devices, where further preferably the rotor axis is sealed against a standing bearing housing via a suitable, preferably non-wearing material seal. The seal can assume various forms and be fitted at various positions. A tapering seal can for example lie directly on the cylindrical shaft. A larger surface pressure of the seal can be achieved for example by a special shaft form or a shoulder firmly connected with the shaft. Here too preferably the dimensioning of the housing or seal has no negative effect on the blood flow, where in particular the proposed cooling effect is highly efficient due to the high blood speeds.

A further preferred embodiment of the invention provides for a multiplicity of pump outflows or outlets which in particular, if these are arranged with their respective openings to the blood chamber arranged radially about their periphery, can reduce the load on the rotor due to the flow effects or flow resistance (in contrast to a single opening); these outlets are particularly suitably implemented by means of spiral housing extensions of a blood pump housing.

It is also particularly advantageous to support the advantageous operating and production properties of the blood pump according to the invention by configuring the pump drive, where according to a preferred embodiment (best mode) the rotor has a closed rotor body, from the outer surface of which extend a multiplicity of rotor blades preferably arranged radially about the periphery of the rotor housing, and where electric and/or magnetic drive elements of the rotor are firmly held inside the rotor body preferably next to the outer surface of the rotor body, and are designed to co-operate with the electrical and/or magnetic drive elements of the blood pump provided in the pump housing surrounding the blood chamber. In particular it is advantageous to design coils as electric drive elements such that the heat generated therein (by electrical resistance) can be dissipated as favourably as possible preferably by the blood flow. This is achieved firstly by a close contact with the housing wall on the blood side and thermal insulation due to air or a filling on the back of the coil. Between the coil and the thermal insulation is a casing of ferromagnetic material to concentrate the magnetic field. Equally preferably coils are provided with a multiplicity of windings and either these are structured separately controllable for the purpose of redundancy or the separate individual windings are designed controllable for the purposes of controlling the power of the pump by suitably arranged control electronics.

On the basis of the control or power control of the pump, there are further numerous advantageous refinement possibilities in the sense that the blood pump according to the invention can be regarded as a regulated system according to a further advantageous refinement. The means provided according to the refinement for measuring the blood stream, pressure and/or flow of the blood can preferably co-operate with means for detecting the rotation speed and/or power of the pump so that by suitable combination along or on the basis of a pump curve, an independent load adaptation is possible to the relevant condition of the patient as measured by the parameters of the flowing blood.

Finally this approach is based on a comprehensive, transcutaneous energy and information transfer system which with the help of preferably wireless communication means also allows communication with external monitoring and control equipment. This gives the patient the greatest possible freedom without losing the necessary medical control.

As part of the possibilities for refinement of the invention by suitable configuration of allocated control electronics, it is also possible to take into account further relevant control parameters such as ECG signals, which particularly preferably can be detected according to a refinement by any existing cardiac pacemaker and are available for electronic processing, and thus ensure an integral pump control which to a great extent is dependent on current parameters or function values of the heart to be supported; for the possible combination of a pump control with a control unit for a cardiac pacemaker as part of the present invention, going beyond the concrete applications as part of the present invention, independent protection is also claimed.

As a result the present invention can serve to improve significantly current pumps for non-pulsatile cardiac support in regard to both operating safety and also the potential risk to the patient from thrombosis formation, without excessive design complexity. Furthermore the present invention is characterised additionally by simple manufacture and non-problematical mechanical tolerance behaviour, so that it can be assumed that with the present invention additional patient groups and areas of application can be found.

Further advantages, features and details of the present invention arise from the description below of preferred embodiment examples and using the drawings. These show.

Figure 1:
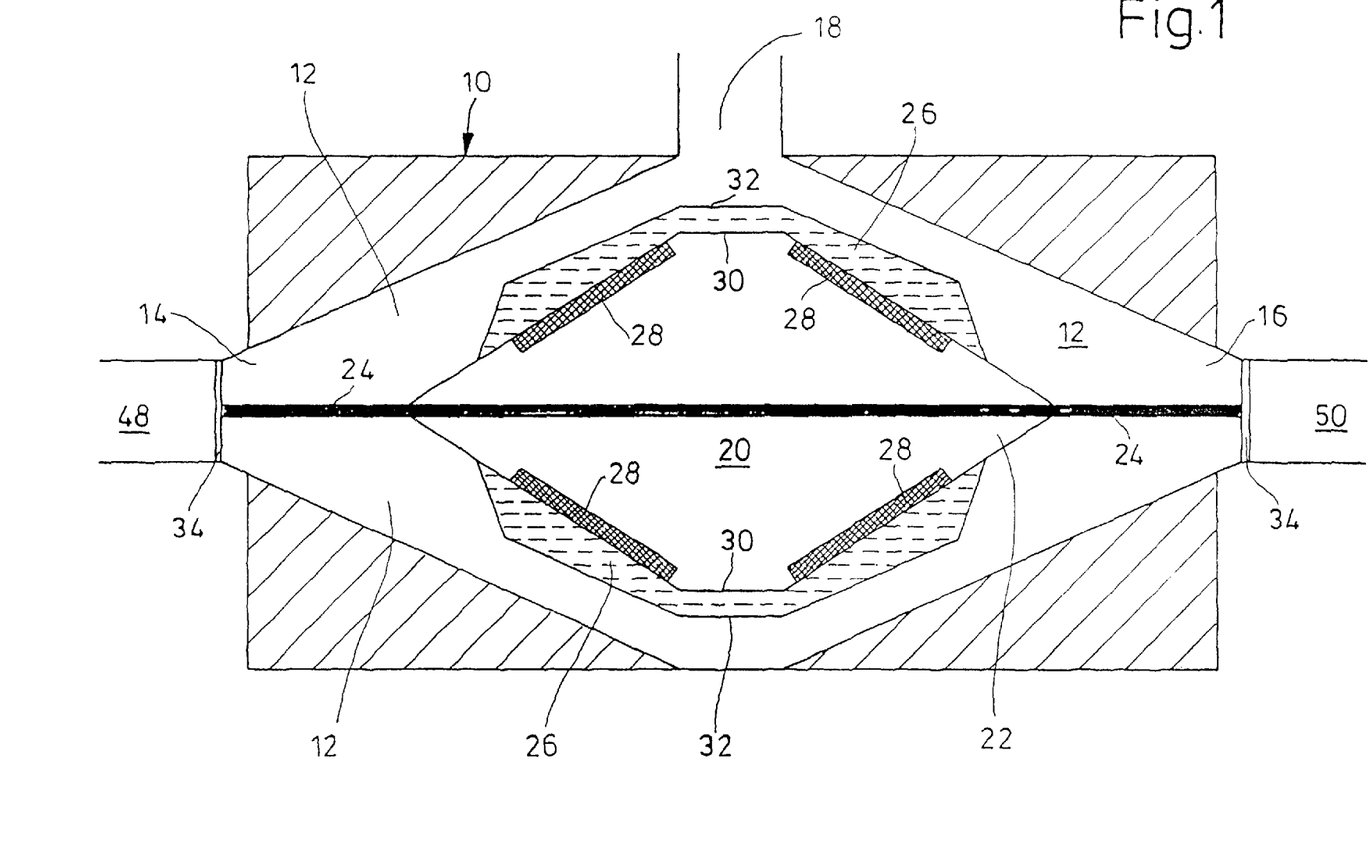
FIG. 1: a diagrammatic side section view in axial direction of the rotor shaft of a first preferred embodiment of the present invention (best mode)
Figure 2:
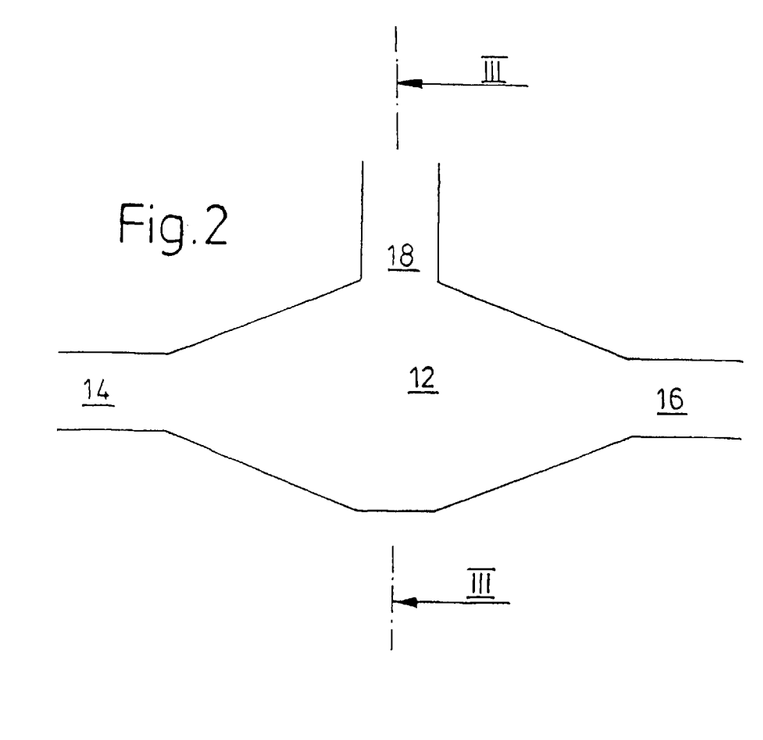
FIG. 2: a diagrammatic view of a longitudinal section through the blood chamber of the embodiment in FIG. 1.
Figure 3:
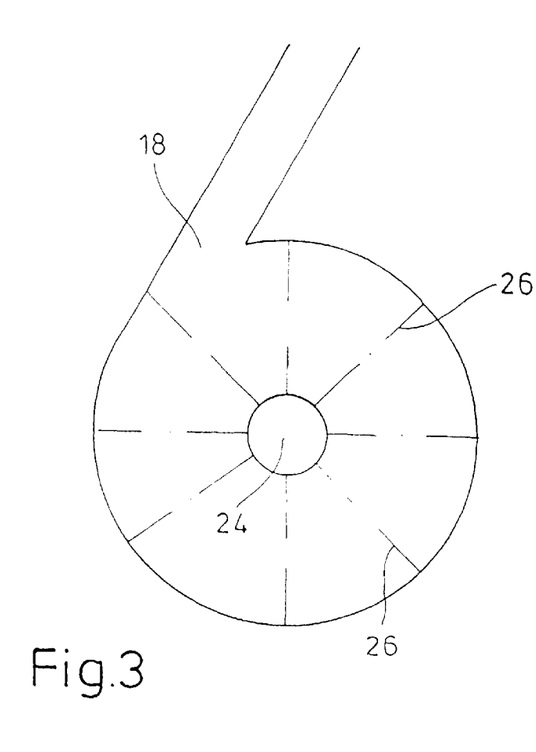
FIG. 3: a section view along section line III—III in FIG. 3.
Figure 4:
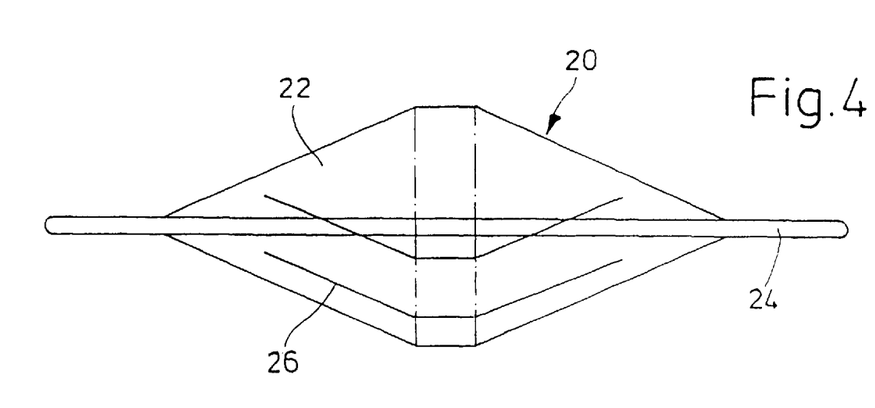
FIG. 4: a diagrammatic side view of the rotor of the embodiment in FIG. 1.
Figure 5:
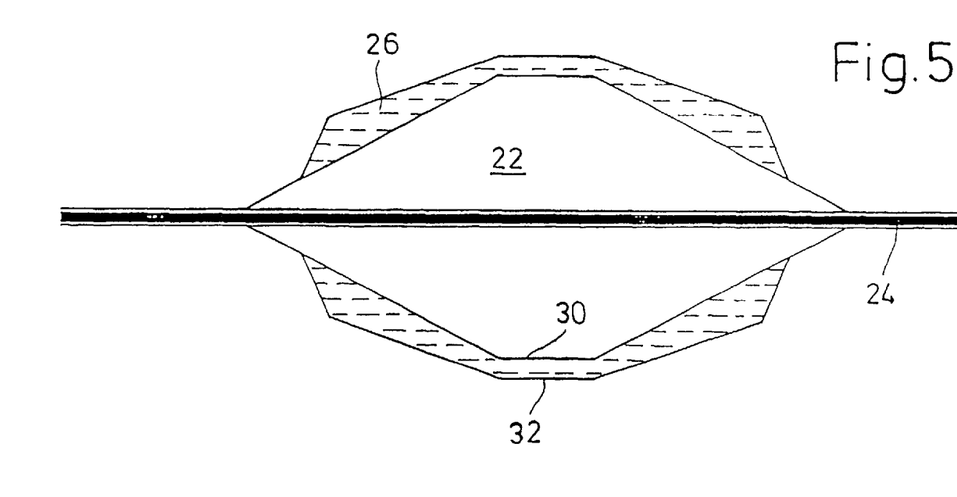
FIG. 5: a section view through the rotor.

A blood pump shown diagrammatically with cylindrical pump housing 10 according to a first embodiment of the present invention has ill the pump housing 10 an essentially octagonal blood chamber 12 in the axial section view shown, which in the manner of a double cone forms at both ends, at pointed ends, a left 14 and right inlet 16 and—as is particularly clear in the section view in FIG. 3—in the centre area (namely the greatest diameter of the double cone) opens into an outlet extending essentially tangentially in the peripheral direction.

As can be seen diagrammatically in the view in FIG. 1, a rotor 20 consisting of an also double-conical rotor body and a rotor shaft (rotor axis) 24, which extends through the opposite pointed end sections of the rotor body 22, is mounted in the blood chamber 12 in the area of the left inlet 14 and the right inlet 16 so that blood flowing in through the inlets 14 and 16 can flow essentially evenly at the ends around the rotor shaft 24, contact the rotor body 22 and be driven centrifugally outwards by the effect of six rotor blades 26 arranged distributed radially about the periphery of the rotor body 22, and be accelerated in the outlet direction through a clear or free flow cross-section reducing continuously in the direction of the outlet 18 between the pump housing 10 and rotor body 22.

The rotor 22 is driven by rotor magnets 28 which are arranged inside the rotor body 22 below its surface and co-operate with drive elements of a pump motor, which—not shown in the figures—are provided in the pump housing opposite the rotor magnets 28.

Due to the geometric conditions described above and shown in FIG. 1, the mechanical design of the blood pump of the embodiment shown allows a particularly gentle, atraumatic although efficient transport of blood entering through the inlets 14, 16: as can be seen particularly clearly in FIG. 1, the double-conical rotor body 22 with its tapering end sections first begins a predetermined distance in front of the allocated inlet ends; with a typical external diameter of the pump housing of 35 mm and an example length of around 70 mm, this distance on each side is 10 to 12 mm. This distance allows the blood flowing through the relevant inlets to flow first with low turbulence and essentially laminar in the direction of the rotor shaft, and in particular avoids the effects of a centrifugal acceleration or crushing of blood constituents on the inlet side due to the rotor shaft movement at the inlet concerned. A further measure which has positive effect on the atraumatic action of the arrangement shown consists of the design of the left and right inlet geometry in relation to the outlet: as can be seen in FIG. 1, the cumulative inlet cross-section of the two inlets 14, 16 is greater than the effective flow cross-section of the outlet 18 (or the effective ventricular supply flow cross-section). This means that due to the gradual expansion of a flow cross-section of a connected inlet flow cannula towards the inlet, the blood flow can gradually be slowed and thus has a less traumatic effect on the blood.

As can also be seen from FIG. 1, both a flattening 30 in the centre area of the rotor body 22 and a flattening 32 in the peripheral end area of the rotor blades 26 are formed, where in the axial direction these flattened areas 30, 32 each correspond to the axial extension of the outlet cross-section; this measure too serves for atraumatic flow optimisation in the described embodiment.

Advantageously according to the invention the rotor shaft 24 is rotatably mounted at both ends on bearings 34 (shown purely diagrammatically in FIG. 1) where due to the symmetrical blood supply through the two inlets 14, 16, an axial force exerted on both sides of the rotor 20 compensates for itself in the ideal case where there is identical pressure of the incoming blood, in normal cases the only slight pressure differences however lead to an extremely low axial load on the bearing pair 34. The result is an extremely long life of the bearing arrangement to be described below in more detail. For the sake of completeness however it should be explained that the arrangement of the magnets 28 in the rotor body 22, clearly evident from FIG. 1, allows simple and precise balancing of the rotor in the radial direction so that in this direction too the loads acting on the bearing 34 are minimised.

Figure 6:
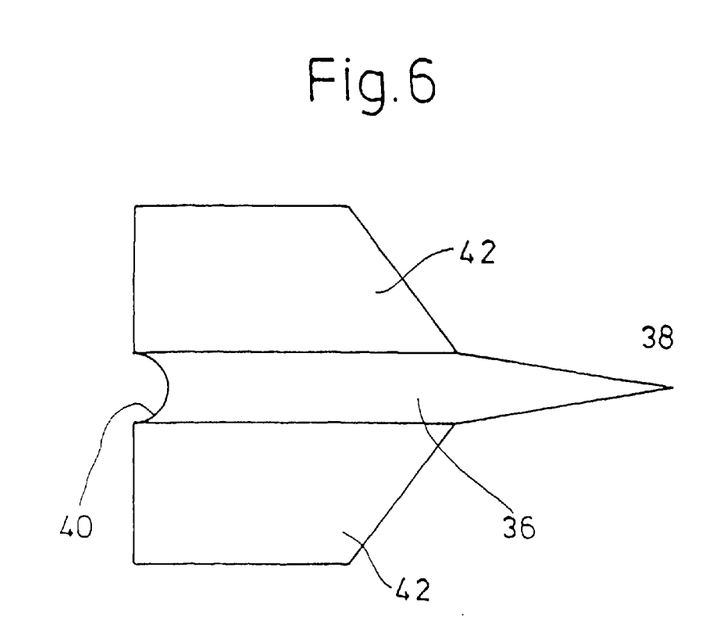
FIG. 6: a side view of a flow regulator on the inlet side for use with the embodiment in FIG. 1.
Figure 7:
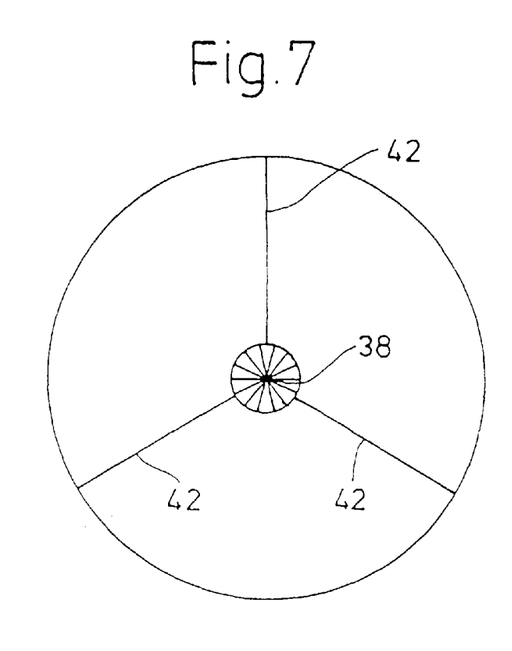
FIG. 7: a view of the flow regulator (used) according to FIG. 6 from the inlet side direction.

FIGS. 6 and 7 show flow regulators 36 which can be provided according to a preferred refinement on the inlet side as a flow guidance device which, in the side view in FIG. 6, have a tip 38 tapering in the direction of the incoming blood flow, at the opposite end form a bearing shell 40 to hold the rotor shaft 36 and carry three fins 42 extending radially and distributed about the periphery of the regulator element 36, which as is particularly clear viewed from the supply direction in FIG. 7, together with the tip 36 form an only minimal flow resistance for the incoming blood stream, on the contrary in the peripheral direction can effectively prevent the occurrence of turbulence or similar (in particular also due to turbulence effects at the inlet concerned).

The front surfaces of the fins have a taper whereas in the embodiment example shown the back surfaces terminate flush with the central carrier element of the flow regulator 36. The tapering front surfaces are particularly suitable for avoiding thrombus formation as the blood flow is diverted in an orderly manner and with low turbulence about the central carrier element of the flow regulator 36 and the fins, and due to the geometry shown there are only minimal areas with backflow and blood turbulence behind the flow regulator.

In concrete terms as shown in FIG. 7 a flow regulator 36 is introduced into each of the inlets 14, 16, there makes contact with the pump housing 12 and at the same time by means of the bearing shell 40 provides a mounting for the pump shaft which is subjected to low load due to the symmetry and is also durable.

Figure 8:
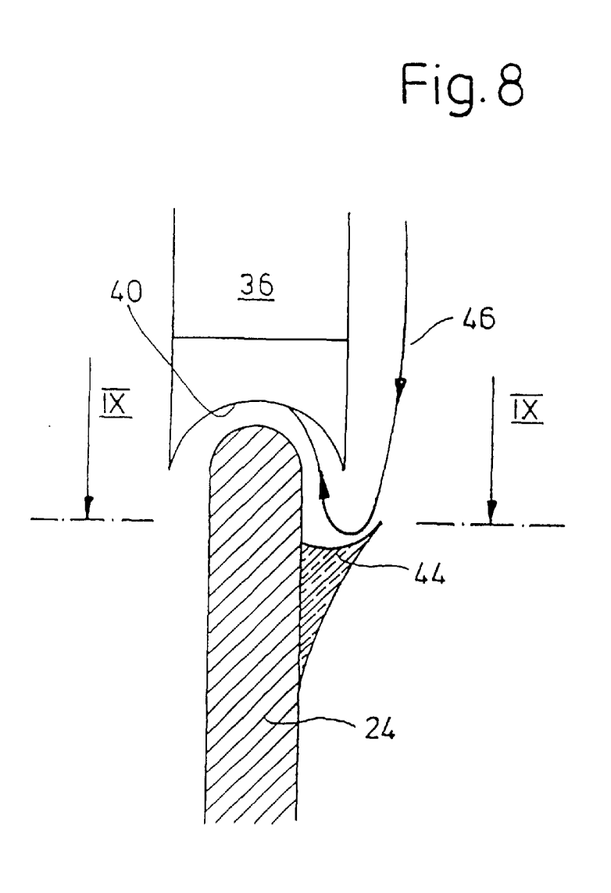
FIG. 8: a diagrammatic side view of a shaft mounting in the inlet area with flushing lip and diagrammatically indicated diversion of the blood flow for flushing purposes.
Figure 9:
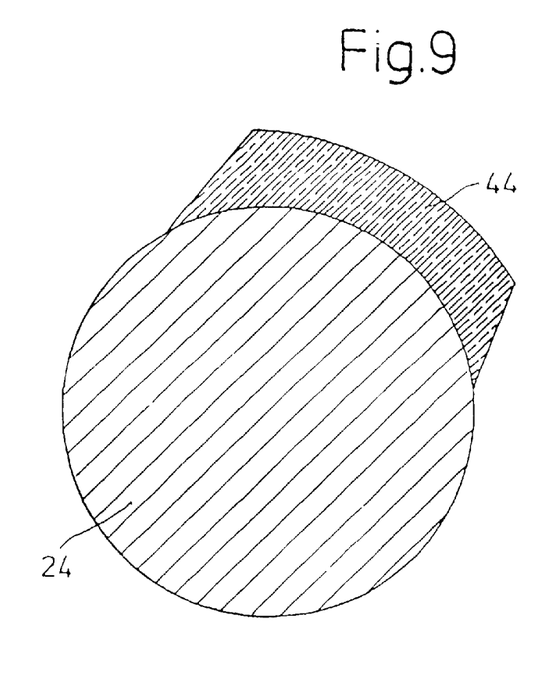
FIG. 9: a section view inside the section line IX—IX in FIG. 8.

According to a further advantageous refinement of the invention it is also possible to flush the bearing formed between the bearing shell 40 and the rounded end of the rotor shaft 24 by the incoming blood: as FIGS. 8 and 9 show, namely at the end on the rotor shaft 24 is formed a projection of the manner of a flushing lip 44 which, as clarified by the flow line 46, deflects part of the blood flowing in through the inlet in the direction of the bearing shell 40 and thus ensures a reliable flushing of the bearing.

Figure 10:
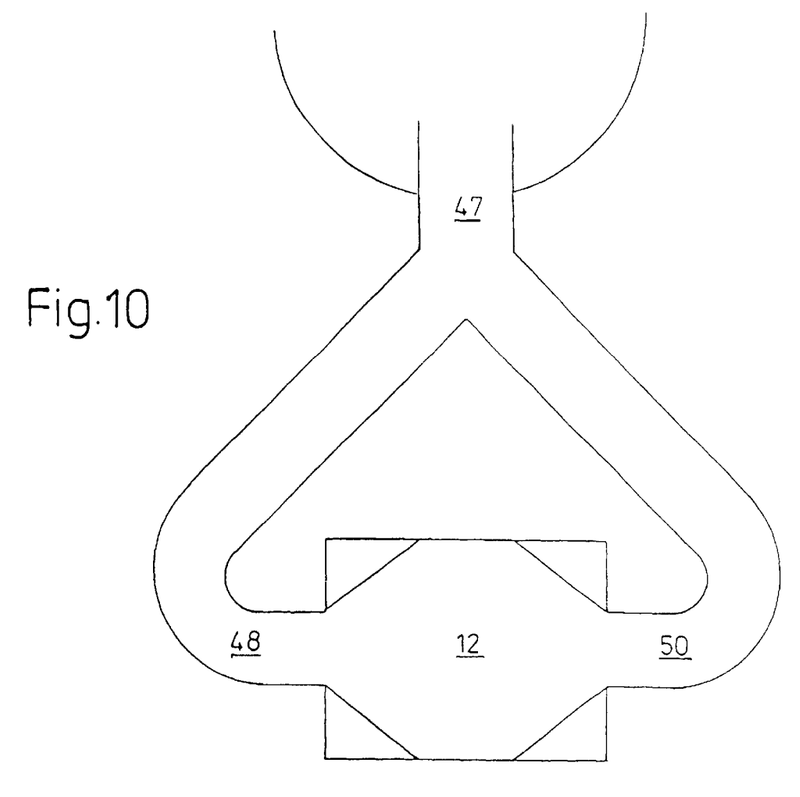
FIG. 10: a diagrammatic view of the left and right side inlet cannulae for connecting the pump according to FIG. 1 with the common inlet cannula of the ventricle.

FIG. 10 shows the inlet side connection of the pump housing 10 with the ventricle by means of a left and a right inlet cannula 48, 50, which to minimise pressure fall are guided in a relatively large radius in the body of the patient and preferably formed as a rigid system (alternatively flexible or a combination of both).

As shown in FIG. 10 in concrete terms the inlet cannula consists of a large calibre, singular cannula 47 which is inserted in the left ventricle and has a flow divider (not shown). In use, implanted directly below the heart or diaphragm, this cannula 47 splits into two equal calibre, equal length inlet cannulae 48, 50 which supply the blood to the pump and blood chamber in the greatest possible curve. Thus the division of the common cannula 47 should be as pointed as possible to achieve a homogeneous division of the blood, so that again the pump receives almost the same blood volumes and pressures at the left inlet 14 and right inlet 16. Not shown in detail in FIG. 10 is the outlet 18 which tangentially starts from the centre area of the pump housing 10 (FIG. 3); in this area of the pump both the pressure and the blood speed are at their greatest. Accordingly here a connection for an outlet cannula (not shown) should have the greatest possible diameter in order to guarantee a slowing of the blood; this is preferably achieved by a conical form with increasing cross-section radii.

The pump housing 10 shown purely diagrammatically in FIG. 1 in addition holds the control electronics for the motor, where the system can then be supplied with energy from an implanted battery (particularly preferably the battery is charged by means of transcutaneous energy transfer). Via this supply port also current operating data of the pump can be read and passed for external further processing in order to influence the pump control. According to a refinement namely it is provided to control the output of the pump by means of an electromagnetic flow meter which is preferably applied to the outlet cannula from the outside; a further flow meter measures the blood flow inside the pulmonary artery. The control unit allocated to the pump establishes flow differences and uses these to regulate the pump so that in particular phenomena of over-pumping with induction of the free ventricular wall or septum, or pump obstruction, can be avoided.

Figures 11, 12:
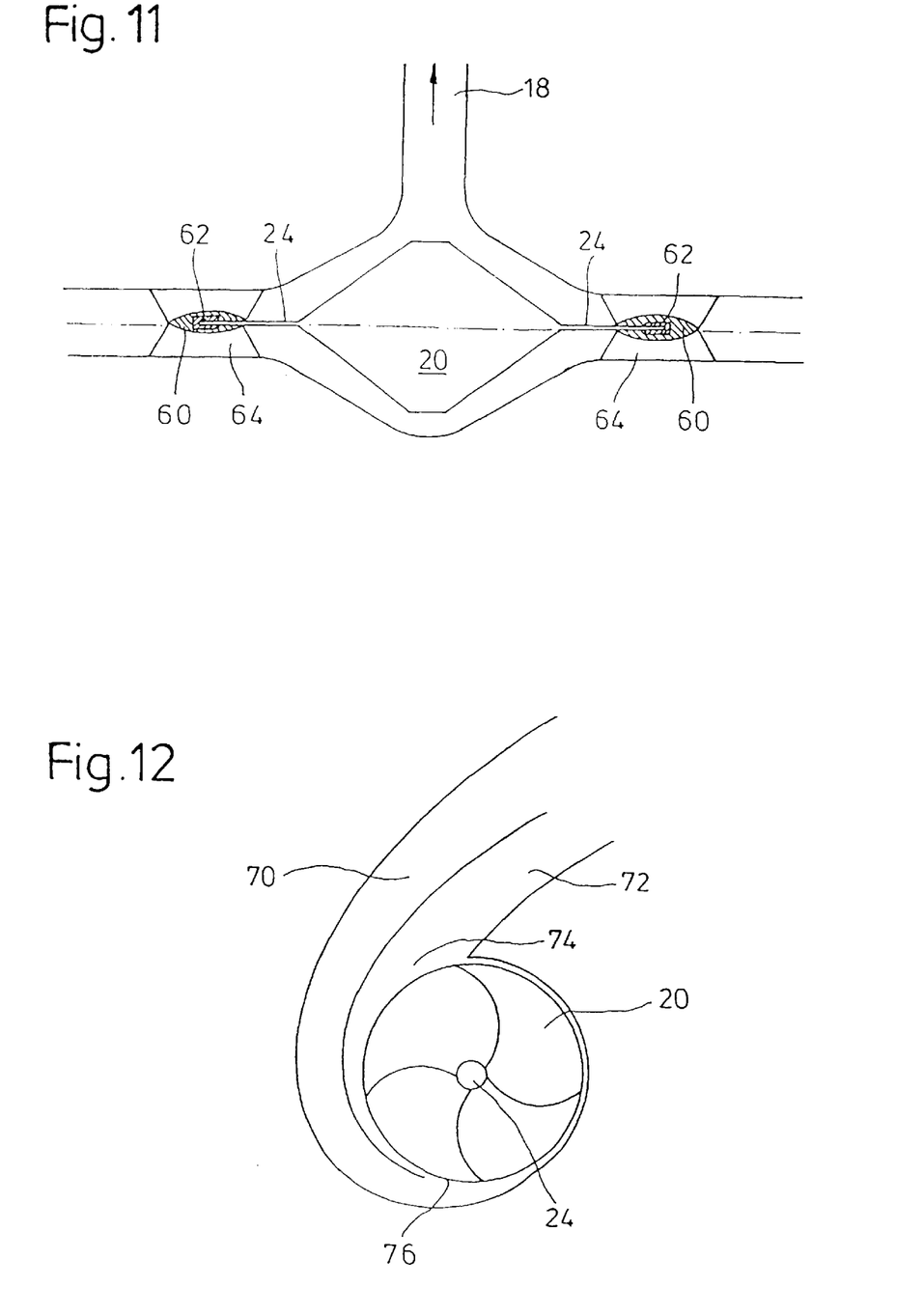
FIG. 11: a diagrammatic side section view of an alternative embodiment with encapsulated sealed bearing housing for mounting the rotor shaft.
FIG. 12: a diagrammatic section view through the rotor body or the pump housing to show an alternative embodiment of the outlet with a multiplicity of spirally arranged channels arranged with their respective openings to the blood chamber on the peripheral side around the blood chamber.

FIG. 11 shows an alternative design of the end mountings for the rotor axis or shaft 24: in each case embedded in a tapered bearing housing 60 designed for favourable flow and made of material with good heat conductivity, the rotor shaft 24 is mounted in suitable slide or roller bearings 62. In the direction of the rotor body is a seal (not shown) of wear-resistant material where preferably a tapered seal can lie directly on the (cylindrical) shaft. By suitable shaping of the bearing housing and seal it can be ensured that there are no negative effects on the blood flow, rather this is preferably utilised to cool the bearing housing (and hence the bearing) effectively.

As can also be seen in FIG. 11 the respective bearing housing 60 is held by a guide device 64 which consists of three internal longitudinally extended vanes arranged axially about the rotation axis. In particular when this guide device has a curvature (in the axial and/or radial direction), the incoming blood flow can be optimised as a degree of prerotation is applied for the subsequent rotor body. Due to the good thermal contact with the bearing housing, they also serve as additional cooling surfaces for the bearing and thus reduce further the local thermal load of the blood.

FIG. 12 show in comparison with FIG. 3 an alternative embodiment of the outlet 18: as can be seen here this embodiment provides a multiplicity of outlet channels 70, 72 which are arranged with their respective openings 74, 76 towards the blood chamber, divided around the periphery. This leads to the rotor being loaded fluidically not merely at one peripheral point by a flow resistance connected with the outlet, but as shown in FIG. 12 two or more openings are provided preferably distributed about the periphery. The individual outlet channels 70, 72 then suitably merge downstream.

The present invention is not restricted to the embodiment examples described, rather further preferred alternatives and/or refinements are provided which in practical terms further promote the atraumatic effects of the pump. These include for example the cross-section design of the rotor blades 26 for which a rounding is suitable at the ends, in particular in the full radius.

A further variant of the mechanically effective mounting of the rotor axis (rotor shaft) consists in that the flow guidance device according to the invention in the inlet connectors forms a fixed shaft (more precisely a shaft shoulder) on both sides of the blood chamber which project into the blood chamber. A tip of this fixed shaft shoulder then forms a bearing part for a bearing shell provided on the rotor which co-operates with the shaft shoulder.

In this way a mechanically active bearing is achieved which can project into the blood chamber. With this it is possible that the bearing can be Hushed with blood flowing at high pressure from the inlet: a flushing lip or similar guide element is no longer required.

As a result with the geometry described not only is an atraumatic gentle treatment of the incoming blood achieved (and hence largely an avoidance of thrombosis formation) but also the haemodynamic efficiency is so high that operating speeds of around 2000 rpm can be maintained, considerably below the rotation speed of existing pump systems. This again is expressed in the long life and resistance to fault.

Whereas in the embodiment example described the bearing arrangement subject to wear, consisting of a rotor shaft and bearing shell, is usually made of hard abrasion-resistant material—precious stones are particularly suitable for the bearing shell and/or tip of the rotor shaft, whereas the shaft itself is typically made of ceramic—naturally the use of other suitable materials also lies within the scope of the expert in the field.

What is claimed is:

1. A blood pump comprising:
   a pump housing (10) defining a chamber (12); a rotor (20) rotatably mounted in the chamber about a rotor axis (24); inlets (14, 16) provided on opposing ends of the chamber along the rotor axis (24) wherein the inlets are connected to an inlet cannula (48, 50); an outlet (18) from the chamber, the outlet connects with an outlet cannula and extends in a direction substantially perpendicular to the rotor axis (24), wherein the rotor is mounted for rotation about rotor axis (24) in bearings (34, 40) connected to the pump housing (10) in the area of the inlets (14, 16).

2. A blood pump according to claim 1, wherein the chamber (12) is formed as a double cone.

3. A blood pump according to claim 1, wherein at least one of the bearings (34, 40) include turbulence prevention means.

4. A blood pump according to claim 1, wherein the bearings (34, 40) having a flushing lip (44) so that they can be flushed by blood flowing through the inlets (14, 16).

5. A blood pump according to claim 1, wherein the outlet (18) has a multiplicity of outlet channels (70, 72) each of which has an opening (74, 76) to the chamber.

6. A blood pump according to claim 1, wherein the bearings (62) have a bearing housing (60) are cooled by incoming blood.

* * * * *